(12) United States Patent
Stas et al.

(10) Patent No.: US 10,668,312 B2
(45) Date of Patent: Jun. 2, 2020

(54) CONTROLLED MEDICATION DENATURING COMPOSITION

(71) Applicant: Okra Medical, Inc., John's Island, SC (US)

(72) Inventors: Justin Stas, John's Island, SC (US); Yizhong Wang, Ann Arbor, MI (US); Evan Boyst, Belleville, MI (US); Venkata S. Reddy Channu, Ypsilanti, MI (US); Emma Leishman, Ann Arbor, MI (US)

(73) Assignee: Okra Medical, Inc., Johns Island, SC (US)

( * ) Notice: Subject to any disclaimer, the term of this patent is extended or adjusted under 35 U.S.C. 154(b) by 0 days.

(21) Appl. No.: 16/456,958

(22) Filed: Jun. 28, 2019

(65) Prior Publication Data

US 2020/0108286 A1   Apr. 9, 2020

Related U.S. Application Data

(63) Continuation of application No. PCT/US2019/037742, filed on Jun. 18, 2019.

(60) Provisional application No. 62/792,762, filed on Jan. 15, 2019, provisional application No. 62/740,625, filed on Oct. 3, 2018.

(51) Int. Cl.
| | |
|---|---|
| *A62D 3/38* | (2007.01) |
| *A62D 101/22* | (2007.01) |
| *A62D 101/28* | (2007.01) |
| *A62D 101/26* | (2007.01) |

(52) U.S. Cl.
CPC ............ *A62D 3/38* (2013.01); *A62D 2101/22* (2013.01); *A62D 2101/26* (2013.01); *A62D 2101/28* (2013.01)

(58) Field of Classification Search
CPC ........................................................ A62D 3/38
USPC ........................................................ 588/320
See application file for complete search history.

(56) References Cited

U.S. PATENT DOCUMENTS

| | | | |
|---|---|---|---|
| 8,785,712 | B2 | 7/2014 | Deryck et al. |
| 9,044,377 | B2 | 6/2015 | Maness |
| 2007/0014839 | A1 | 1/2007 | Bracht |
| 2012/0088951 | A1 | 4/2012 | Deryck et al. |
| 2014/0187842 | A1 | 7/2014 | Holaday et al. |
| 2014/0235917 | A1 | 8/2014 | Best |
| 2015/0265867 | A1 | 9/2015 | Sarangapani |
| 2018/0001357 | A1 | 1/2018 | Schestopol et al. |
| 2019/0126331 | A1 | 5/2019 | Vanderwoude et al. |

FOREIGN PATENT DOCUMENTS

| | | |
|---|---|---|
| EP | 2760412 B1 | 7/2017 |
| GB | 2527885 A | 6/2016 |
| JP | 4474622 | 6/2010 |
| WO | 2013171516 A1 | 11/2013 |

OTHER PUBLICATIONS

Article entitled: Using Ozonation-Hydrolysis Acidification to the Pharmaceutical Tail Wastewater Pretreatment by Yanjiao Gao and Runzhu Huang, in Water Practice & Technology vol. 10 No. 4, 2015, Dec. 2015; pp. 688-694 Dec. 2015.

*Primary Examiner* — Edward M Johnson
(74) *Attorney, Agent, or Firm* — Christopher S. Dodson; Nexsen Pruet, PLLC

(57) ABSTRACT

A composition for decomposing pharmaceutically active agents, comprises up to 30 wt. % oxidizer; and up to 30 wt. % immobilizer; wherein the wt. % is based on a total weight of the composition.

13 Claims, No Drawings

CONTROLLED MEDICATION DENATURING COMPOSITION

CROSS-REFERENCE TO RELATED APPLICATIONS

This application claims priority under 35 U.S.C. § 119 to U.S. Provisional Patent Application No. 62/792,762, filed Jan. 15, 2019, and to U.S. Provisional Patent Application No. 62/740,625, filed Oct. 3, 2018, the entireties of which are incorporated by reference herein.

FIELD

This disclosure is generally related to hazardous waste disposal, and, more specifically, to the disposal of controlled substances and medications.

BACKGROUND

The leading cause of accidental death in U.S. is drug abuse. Over one hundred people die daily from opioid-related drug overdoses in the U.S. alone. A total of 42,249 people died from overdosing on opioids in 2017 alone. In addition, over two million Americans are currently struggling with opioid dependency and 11.4 million Americans misused prescription opioids. In addition, many of these medications find their way into the environment and drinking water.

The source of many of these drugs come from prescription drugs that were used by those other than the patient for whom they were intended. Often unused medications are left in drawers or medicine cabinets, or just discarded in trash bins. Some are flushed down toilets.

There is no current method of safe disposal that is environmentally safe and completely denatures controlled substances at home or in hospitals. Moreover, diversion of opioid-related drugs among healthcare professionals is a growing problem. Among health care providers, 15% of pharmacists, 10% of nurses, and 8% of physicians may have either alcohol dependency or drug dependency of both.

An effective way to dispose of unwanted or unused medications would help to avoid those medications from being abused. There are a number of commercial products that purport to degrade these medications, such as Rx Destroyer™, Drug Buster™, Narc-X™, Pill Terminator™, Element MDS™, Cactus Smart Sink™, Mallinckrodt MDS™, Pill Catcher™, Stericycle™, and the like. However, while many of these products offer some ability to degrade controlled substances, none of them provide a universal solution and very few are able to reach close to 100% degradation of any controlled substances, much less most or all controlled substances.

Consequently there is still a very large unmet need for an effective way to generally degrade controlled substances, and, ideally, universally degrade controlled substances.

SUMMARY

In an aspect, compositions for decomposing pharmaceutically active agents are described here. In some embodiments a composition comprises up to 30 wt. % oxidizer; and up to 30 wt. % immobilizer; wherein the wt. % is based on a total weight of the composition. The oxidizer comprises one or more of a permanganate, a peroxide, a halogenated oxidant, hypochlorite salts, nitric acid, sulphuric acid, hydrochloric acid, sodium perborate tetrahydrate, sodium pyrophosphate tetrabasic, or mixtures thereof. The permanganate can comprise potassium permanganate, calcium permanganate, or both. The peroxide comprises hydrogen peroxide in some cases. The halogenated oxidant comprises sodium dichloroisocyanurate dihydrate, sodium dichloroisocyanurate, potassium dichloroisocyanurate dihydrate, trichloroisocyanuric acid, dichloroisocyanuric acid, or any combination thereof in some instances.

In some embodiments, the oxidizer comprises potassium permanganate and sodium dichloroisocyanurate dehydrate. The potassium permanganate is present from between 0.1 to 8 wt. %, and the sodium dichloroisocyanurate dehydrate is present from between 0.1 to 25 wt. % of the total weight of the composition in some instances.

In some cases, the oxidizer comprises potassium permanganate, sodium dichloroisocyanurate dehydrate, and trichloroisocyanuric acid. The potassium permanganate is present from between 0.1 to 8 wt. %, the sodium dichloroisocyanurate dehydrate is present from between 0.1 to 25 wt. %, and the trichloroisocyanuric acid is present from 0.1 to 7 wt. % of the total weight of the composition in some instances.

An immobilizer described herein can comprise a gelatin, an agarose, a starch, a vegetable gum, a cellulose, a cellulose derivative, a carbomer, a polyvinylpyrrolidone, polyethylene oxide, polyethylene glycol, an alginate, guar gum, xanthan gum, a saccharide, an amylopectin, Arabic gum, a polyacrylic acid, or any combination thereof in some embodiments. In a particular embodiment, the immobilizer comprises xanthan gum. The xanthan gum can comprise up to 30 wt. % of the composition in some cases.

In some embodiments, compositions described herein further comprise a multivalent alkaline earth metal-based chloride. The multivalent alkaline earth metal-based chloride can be $CaCl_2$, $MgCl_2$, $BaCl_2$, or mixtures thereof in some instances. In some cases, the alkaline earth metal-based chloride comprises up to 5 wt. % of the composition.

In some embodiments, compositions described herein further comprise a solidifier comprising a clay, a fumed silica, a sand, or any combination thereof. The clay can be present up to 25 wt. %; the fumed silica can be present up to 25 wt. %; and/or the sand can be present up to 25 wt. %.

In further embodiments, compositions described herein can further comprise a hydrolytic agent. Exemplary hydrolytic agents include potassium hydroxide, sodium hydroxide, lithium hydroxide, or combinations thereof. In some cases, the hydrolytic agent comprises 0.1 to 40 wt. % of the total composition.

In another embodiment, a controlled substance degrading composition comprises potassium permanganate; sodium dichloroisocyanurate dehydrate; and an immobilizer. The potassium permanganate can be present up to 8 wt. %, and the sodium dichloroisocyanurate dehydrate can be present up to 25 wt. %, the wt. % being based on a total weight of the composition. In some cases, the immobilizer can be present up to 30 wt. %, the wt. % being based on a total weight of the composition.

In some embodiments, the immobilizer comprises a gelatin, an agarose, a starch, a vegetable gum, a cellulose, a cellulose derivative, a carbomer, a polyvinylpyrrolidone, polyethylene oxide, polyethylene glycol, an alginate, guar gum, xanthan gum, a saccharide, an amylopectin, Arabic gum, a polyacrylic acid, or any combination thereof.

In another embodiment, the controlled substance degrading composition further comprises trichloroisocyanuric acid. The trichloroisocyanuric acid can be present up to 7 wt. %, the wt. % being based on a total weight of the composition.

In some embodiments, the controlled substance degrading composition further comprises a clay, a fumed silica, a sand, or mixtures thereof. The clay can be present up to 25 wt. %; the fumed silica can be present up to 25 wt. %; and the sand can be present up to 25 wt. %.

In some cases, the controlled substance degrading composition further comprises up to 7 wt. % of $CaCl_2$.

In some embodiments, the controlled substance degrading composition further comprises a hydrolytic agent. The hydrolytic agent can comprise potassium hydroxide, sodium hydroxide, lithium hydroxide, or combinations thereof. The hydrolytic agent comprises 0.1 to 40 wt. % of the total composition in some instances.

In another aspect, a method of degrading a pharmaceutically active ingredient is described. The method of degrading a pharmaceutically active ingredient comprises placing the pharmaceutically active ingredient in any composition described herein; and degrading the pharmaceutically active ingredient. The pharmaceutically active ingredient can in some cases be a US Drug Enforcement Agency identified schedule I, II, and/or III controlled substance. In some embodiments, degrading the pharmaceutically active ingredient comprises rendering the pharmaceutically active ingredient non-retrievable as defined by the US Drug Enforcement Agency under 21 C.F.R. § 1300.05. In some instances, the pharmaceutically active ingredient is degraded within two hours after being placed in the composition.

The method of degrading the pharmaceutically active ingredient can in some cases further comprise adding water to any composition described herein.

DETAILED DESCRIPTION

Embodiments described herein can be understood more readily by reference to the following detailed description, examples, and drawings. Elements, apparatus and methods described herein, however, are not limited to the specific embodiments presented in the detailed description, examples, and drawings. It should be recognized that these embodiments are merely illustrative of the principles of this disclosure. Numerous modifications and adaptations will be readily apparent to those of skill in the art without departing from the spirit and scope of this disclosure.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

All wt. % quantities are based on a total weight of the composition unless expressly stated otherwise.

According to its major aspects and briefly described, compositions disclosed herein can irreversibly degrade Schedule I, II, and/or III controlled substances, as identified and defined by the US Drug Enforcement Agency ("DEA") in 21 CFR §§ 1308.11 (Schedule I), 1308.12 (Schedule II), and § 1308.14 (Schedule III), each of which is incorporated by reference in their entireties. Exemplary controlled substances under Schedules I, II, and III comprise fentanyl, sufentanil, hydromorphone, morphine, remifentanil, meperidine, methadone, midazolam, lorazepam, diazepam, ketamine, hydrocodone, oxycodone, codeine, nalbuphine, butorphanol, cocaine, heroin, ecstasy, amphetamine, methamphetamine, methohexital, pentobarbital, THC, propofol, ketamine, glycopyrrolate, or any of the other controlled substance listed in Schedule I, Schedule II, or Schedule III. These listed controlled substances are merely exemplary and are not meant to be an exhaustive list, but, rather, a listed to illustrate a small sampling of the large number of controlled substances listed in these Schedules. The composition is not limited only to degrading these controlled substances though, but can in some embodiments degrade any substance not inconsistent with the objectives of this disclosure, such as any prescription, nonprescription over-the-counter drug or medication, illicit/illegal substances, or Schedule IV and Schedule V controlled substances as identified and defined by the DEA in 21 CFR §§ 1308.14 (Schedule IV) and 1308.15 (Schedule V). Again, these examples are not exhaustive, but are being listed merely to provide illustrations of a few of the Schedule I, II, III, IV, and V substances, prescription drugs and medications, illicit/illegal substances, and over-the-counter drugs or medications that can be degraded by compositions and methods described herein. For purposes herein, all substances discussed in this paragraph will collectively and generally be referred to as "controlled substances," "pharmaceutically active agents," and/or "pharmaceutically active ingredients".

In some embodiments, compositions described herein can irreversibly degrade controlled substances, meaning that the chemical structure of the controlled substance has been modified in such a manner that its chemical structure has been fundamentally changed and cannot routinely or easily being chemically changed back to that of the original controlled substance.

Furthermore, in some embodiments, compositions described herein can render controlled substances "non-retrievable" as defined by the DEA under 21 C.F.R. § 1300.05, which defines non-retrievable as meaning "for the purpose of destruction, the condition or state to which a controlled substance shall be rendered following a process that permanently alters that controlled substance's physical or chemical condition or state through irreversible means and thereby renders the controlled substance unavailable and unusable for all practical purposes. The process to achieve a non-retrievable condition or state may be unique to a substance's chemical or physical properties. A controlled substance is considered "non-retrievable" when it cannot be transformed to a physical or chemical condition or state as a controlled substance or controlled substance analogue. The purpose of destruction is to render the controlled substance(s) to a non-retrievable state and thus prevent diversion of any such substance to illicit purposes." In some instances, the US Food and Drug Administration (FDA) uses the term "non-recoverable" interchangeably with the DEA term "non-retrievable". For purposes herein, the terms "non-recoverable" and "non-retrievable" are assumed to be equivalent and interchangeable, and compositions described herein can render controlled substances both "non-recoverable" and "non-retrievable" as understood by the FDA and DEA, respectively.

Moreover, in some embodiments, compositions disclosed herein can reduce the amount of controlled substances that end up in waterways and drinking water. In some instances, compositions disclosed herein can reduce the amount of controlled substances disposed of in sinks and drains. In some cases, the disclosed compositions can reduce risks of spillage by solidifying the degraded controlled substances. Moreover, since the compositions irreversibly degrade the controlled substances, use of the disclosed compositions can reduce hauling costs for controlled substances, since the degraded controlled substances do not need to be transported to specialized hazardous waste facilities to be destroyed, and do not require special licenses to transport.

I. Compositions

In an aspect, compositions for decomposing or degrading a controlled substance, a pharmaceutically active agent, and/or a pharmaceutically active ingredient are disclosed herein. In some embodiments, a composition comprises an oxidizer and an immobilizer.

A total amount of oxidizer present in compositions described herein can be 0.1 wt. % to 50 wt. %, based on a total weight of the composition. The oxidizer can be present in the composition as a single oxidizing agent or a mixture of oxidizing agents. In some embodiments, a total amount of oxidizer present in the composition is between 0.1 wt. % to 40 wt. %, 0.1 wt. % to 30 wt. %, 0.1 wt. % to 25 wt. %, 0.1 wt. % to 20 wt. %, 0.1 wt. % to 15 wt. %, 0.1 wt. % to 10 wt. %, 0.5 wt. % to 50 wt. %, 1 wt. % to 50 wt. %, 5 wt. % to 50 wt. %, 8 wt. % to 50 wt. %, 10 wt. % to 50 wt. %, 12 wt. % to 50 wt. %, 15 wt. % to 50 wt. %, 18 wt. % to 50 wt. %, 20 wt. % to 50 wt. %, 25 wt. % to 50 wt. %, 30 wt. % to 50 wt. %, 40 wt. % to 50 wt. %, 5 wt. %, 8 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, or 30 wt. %, based on a total weight of the composition. In a preferred embodiment, a total amount of oxidizer present in the composition is up to 20 wt. %. In a more preferred embodiment, a total amount of oxidizer present in the composition is up to 30 wt. %.

An oxidizer described herein can be any oxidizer or oxidizing agent that is not inconsistent with the objectives of this disclosure, such as a substance that gain electrons and is reduced in a chemical reaction. While not intending to be bound by theory, it is believed that the oxidizer reacts with reducing groups or moieties present in the structures of controlled substances to oxidize the controlled substances and irreversibly degrade the controlled substance's molecular structure.

In some embodiments, the oxidizer comprises one or more of a permanganate, a peroxide, a halogenated oxidant, a hypochlorite salt, nitric acid, sulphuric acid, hydrochloric acid, sodium perborate tetrahydrate, sodium pyrophosphate tetrabasic, or mixtures thereof. In a more preferred embodiment, the oxidizer comprises a permanganate.

The permanganate can comprise potassium permanganate, calcium permanganate, or both. In a preferred embodiment, the oxidizer comprises potassium permanganate. The peroxide can be any peroxide not inconsistent with the objectives of this disclosure, such as hydrogen peroxide. The halogenated oxidant can be any halogenated oxidant not inconsistent with the objectives of this disclosure, such as sodium dichloroisocyanurate dihydrate, potassium dichloroisocyanurate dihydrate, trichloroisocyanuric acid, dichloroisocyanuric acid, or any combination thereof. The halogenated oxidant can in some instances generate hypochlorite when mixed with an aqueous solvent. Hypochlorite salts can comprise sodium hypochlorite, including household bleach, potassium hypochlorite, calcium hypochlorite, or lithium hypochlorite.

In one embodiment, the oxidizer comprises a mixture of potassium permanganate and one or more halogenated oxidants. For example, in some cases the oxidizer comprises a mixture of potassium permanganate and sodium dichloroisocyanurate dehydrate. The potassium permanganate can be present from between 0.1 wt. % to 8 wt. %, 0.3 to 7 wt. %, 0.5 wt. % to 6 wt. %, 0.7 wt. % to 5 wt. %, or 1 wt. % to 4 wt. %, and the sodium dichloroisocyanurate dehydrate can present from between 0.1 to 25 wt. %, 2 wt. % to 23 wt. %, 4 wt. % to 21 wt. %, 6 wt. % to 19 wt. %, or 8 wt. % to 15 wt. % of the total weight of the composition in some cases. In a preferred embodiment, potassium permanganate is present from between 0.1 to 8 wt. %, and the sodium dichloroisocyanurate dehydrate is present from between 0.1 to 25 wt. % of the total weight of the composition.

In another embodiment, the oxidizer comprises a mixture of potassium permanganate, sodium dichloroisocyanurate dehydrate, and trichloroisocyanuric acid. The potassium permanganate can be present from between 0.1 wt. % to 8 wt. %, 0.3 to 7 wt. %, 0.5 wt. % to 6 wt. %, 0.7 wt. % to 5 wt. %, or 1 wt. % to 4 wt. %, the sodium dichloroisocyanurate dehydrate can present from between 0.1 wt. % to 25 wt. %, 2 wt. % to 23 wt. %, 4 wt. % to 21 wt. %, 6 wt. % to 19 wt. %, or 8 wt. % to 15 wt. %, and the trichloroisocyanuric acid can be present from between 0.1 wt. % to 7 wt. %, of the total weight of the composition in some cases. In a preferred embodiment, the potassium permanganate is present from between 0.1 to 8 wt. %, the sodium dichloroisocyanurate dehydrate is present from between 0.1 to 25 wt. %, and the trichloroisocyanuric acid is present from 0.1 to 7 wt. % of the total weight of the composition.

The immobilizer can be present in a composition as a single immobilizing agent or a mixture of immobilizing agents. The immobilizer can in some instances suspend the individual components of the composition, and prevent settling or separation of those individual components. For example, the immobilizer can sometimes form a network or matrix in a solvent having a plurality of "pockets" where portions of the controlled substance and the oxidizer can be present. These portions can in some cases be immobilized or temporarily present together in close proximity in these pockets, permitting the oxidizer time to interact and react with the controlled substance. In some cases, the oxidizer will have additional time to react with the controlled substance when in the presence of an immobilizer as compared to a solution in which no immobilizer is present.

A total amount of immobilizer present in compositions described herein can be between 1 wt. % to 50 wt. %, based on a total weight of the composition. In some embodiments, a total amount of immobilizer present in the composition is between 1 wt. % to 40 wt. %, 1 wt. % to 30 wt. %, 1 wt. % to 25 wt. %, 1 wt. % to 20 wt. %, 1 wt. % to 15 wt. %, 1 wt. % to 10 wt. %, 1 wt. % to 50 wt. %, 5 wt. % to 50 wt. %, 8 wt. % to 50 wt. %, 10 wt. % to 50 wt. %, 12 wt. % to 50 wt. %, 15 wt. % to 50 wt. %, 18 wt. % to 50 wt. %, 20 wt. % to 50 wt. %, 25 wt. % to 50 wt. %, 30 wt. % to 50 wt. %, 40 wt. % to 50 wt. %, 5 wt. %, 8 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, or 30 wt. %, based on a total weight of the composition. In preferred embodiments, a total amount of immobilizer present in the composition is up to 20 wt. % or up to 25 wt. %. In a more preferred embodiment, a total amount of immobilizer present in the composition is up to 30 wt. %.

Any immobilizer not inconsistent with the objectives of this disclosure can be used. In some embodiments, the immobilizer comprises a gelatin, an agarose, a starch, a vegetable gum, a cellulose, a cellulose derivative, a carbomer, polyvinylpyrrolidone, polyethylene oxide, polyethylene glycol, an alginate, guar gum, a saccharide, an amylopectin, Arabic gum, a superabsorbent polymer (SAP), or any combination thereof.

Exemplary vegetable gums and saccharides include xanthan gum, agar, cellulose, guar, locust bean, pectin, starch, alginate, carrageenan, or any other vegetable gum or saccharide not inconsistent with the goals of this disclosure. Exemplary carbomers include homopolymers of acrylic acid, or acrylic acide crosslinked with an allyl ether of pentaerythritol, allyl ether of sucrose, or allyl ether of propylene. Exemplary amylopectins include average molecular weights of 2000-200,000 glucose units (gu), 2000-175,000 gu, 2000-150,000 gu, 2000-125,000 gu, 2000-100,000 gu, 2000-75,000 gu, 2000-50,000 gu, 2000-50,000 gu, 2000-25,000 gu, 2000-15,000 gu, 2000-10,000 gu, 10,000-200,000 gu, 20,000-200,000 gu, 30,000-200,000 gu, 40,000-200,000 gu, 50,000-200,000 gu, 75,000-200,000 gu, 100,000-200,000 gu, 125,000-200,000 gu, 150,000-200,000 gu, 50,000-150,000 gu, 75,000-125,000, or 30,000-110,000 gu. Exemplary superabsorbent polymers include polyacrylic acids; poly(viny alcohol) (PVA); poly(ethylene oxide (PEO); starch-grafted to various copolymers such as a polyacrylamide copolymer; protein-grafted to various copolymers such as a polyacrylamide copolymer; sodium polyacrylate. The superabsorbent polymers can have at least 50,000 molecular units (mu), at least 75,000 mu, at least 150,000 mu, at least 250,000 mu, at least 500,000 mu, at least 750,000 mu, at least one million mu, greater than one million mu, or combinations thereof. Additionally superabsorbent polymers can have low degrees of crosslink density.

In a preferred embodiment, the immobilizer comprises xanthan gum. The xanthan gum can have an average molecular weight range of 100 kDa to 8 MDa, 100 kDa to 5 MDa, 100 kDa to 1 MDa, 100 kDa to 800 kDa, 100 kDa to 600 kDa, 100 kDa to 400 kDa, 100 kDa to 300 kDa, or 100 kDa to 200 kDa. In an embodiment, the xanthan gum comprises up to 40 wt. % of the composition. In a preferred embodiment, the xanthan gum comprises up to 30 wt. % of the composition. In a more preferred embodiment, the xanthan gum comprises up to 25 wt. % of the composition.

Compositions described herein can further comprise a multivalent cation source, such as a divalent, trivalent, or higher valences. While not intending to be bound by theory, multivalent cation sources are believed to form ionic crosslinking with many immobilizers, such as xanthan gum. In many cases, formation of ionic crosslinking reduces the intrinsic viscosity and elasticity of compositions having immobilizers, allowing greater control over the physical properties of the composition, while reducing the amount of immobilizer needed to achieve those physical properties.

In some embodiments, the multivalent cation source is a multivalent alkaline earth metal-based chloride. The multivalent alkaline earth metal-based chloride can comprise $CaCl_2$, $MgCl_2$, $BaCl_2$, or mixtures thereof.

The multivalent cation sources, such as the alkaline earth metal-based chloride, can comprise up to 1 wt. %, up to 2 wt. %, up to 3 wt. %, up to 4 wt. %, up to 5 wt. % or up to 6 wt. % of the composition.

Compositions described herein can further comprise a solidifier. The solidifier can perform one or more functions in the compositions. For example, in some cases, when a solvent has been added to the composition, the solidifier can disrupt the matrix or network formed by the immobilizer, allowing some movement of the oxidizer and controlled substance as compared to being completely immobilized by the immobilizer. Furthermore, in some embodiments, as a solvent is removed or evaporated from the composition after degradation of the controlled substance, the solidifier can form a solid waste comprising the degradation product and any unreacted oxidizer. Formation of this solid waste can assist in the easy disposal of the composition, by reducing or eliminating messy powders and the like.

The solidifier can be present in the composition as a single solidifying agent or a mixture of solidifying agents. A total amount of solidifier present in compositions described herein can be between 1 wt. % to 75 wt. %, based on a total weight of the composition. In some embodiments, a total amount of solidifier present in the composition is between 1 wt. % to 75 wt. %, 1 wt. % to 65 wt. %, 1 wt. % to 55 wt. %, 1 wt. % to 45 wt. %, 1 wt. % to 35 wt. %, 1 wt. % to 25 wt. %, 1 wt. % to 20 wt. %, 1 wt. % to 15 wt. %, 1 wt. % to 10 wt. %, 5 wt. % to 75 wt. %, 10 wt. % to 75 wt. %, 15 wt. % to 75 wt. %, 20 wt. % to 75 wt. %, 25 wt. % to 75 wt. %, 30 wt. % to 75 wt. %, 35 wt. % to 75 wt. %, 40 wt. % to 75 wt. %, 45 wt. % to 75 wt. %, 50 wt. % to 75 wt. %, 55 wt. % to 75 wt. %, 60 wt. % to 75 wt. %, 65 wt. % to 75 wt. %, 5 wt. %, 8 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 26 wt. %, 27 wt. %, 28 wt. %, 29 wt. %, 30 wt. %, 35 wt. %, 40 wt. %, 45 wt. %, 50 wt. %, 55 wt. %, 60 wt. %, 65 wt. %, 70 wt. %, or 75 wt. %, based on a total weight of the composition.

The solidifier can comprise any solidifying agents not inconsistent with the objectives of this disclosure. In some embodiments, the solidifier can comprise a clay, a fumed silica, a sand, or any combination thereof.

Exemplary clays include phyllosilicates, such as bentonite, hectorite, and kaolinite. In some embodiments, the clay is a modified clay having hydrophobic or hydrophilic functional groups. The clay can have an average particle size of 10 nm to 100 µm, 50 nm to 100 µm, 100 nm to 100 µm, 200 nm to 100 µm, 300 nm to 100 µm, 400 nm to 100 µm, 500 nm to 100 µm, 600 nm to 100 µm, 700 nm to 100 µm, 800 nm to 100 µm, 900 nm to 100 µm, 1 µm to 100 µm, 10 nm to 1 µm, 10 nm to 900 nm, 10 nm to 700 nm, 10 nm to 500 nm, 10 nm to 350 nm, 100 nm to 800 nm, 200 nm to 700 nm, 300 nm to 600 nm, or 200 nm to 500 nm. Exemplary silica can comprise fumed silica having a BET surface area of $m^2/g$ of 50-380, 90-380, 130-380, 150-380, 200-380, 255-380, 300-380, 50, 90, 130, 150, 200, 255, 300, or 380. The sand can have an average particle size of 0.25 mm-3.0 mm, 0.5 mm to 1.5 mm, 0.75 mm to 1.25 mm, up to 1 mm, up to 2 mm, up to 3 mm, 0.25 mm to 2 mm, 0.25 mm to 1.5 mm, 0.25 mm to 1.25 mm, 0.25 mm to 1 mm, 0.25 mm to 0.75 mm, 0.5 mm to 3 mm, 1 mm to 3 mm, 1.5 mm to 3 mm, 2 mm to 3 mm or 2.5 mm to 3 mm. In some embodiments, the solidifier can comprise particles having a particle-size distribution that optimizes packing density when a solvent is removed from the composition. For example, several distinct particle sizes can be used to maximize packing density.

In a preferred embodiment, the clay is present up to 25 wt. %; the fumed silica is present up to 25 wt. %; and/or the sand is present up to 25 wt. %.

While in some embodiments the solidifier can assist in the formation of a solid waste product, in other embodiments, the oxidizer and other reactive components will slowly degrade the immobilizer. In those instances, a solid waste product will is not formed. Rather, a liquid waste product is formed as the oxidizer and other reactive components degrade the immobilizer. The rate of degradation of the immobilizer is generally less than a rate of degradation of the controlled substance, although in some cases the rate of degradation for both is approximately equal.

Compositions described herein can optionally further comprise a hydrolytic agent. A hydrolytic agent described herein can be any compound that generates hydroxide ions ($OH^-$) that is not inconsistent with the objectives of this disclosure. In some embodiments, a hydrolytic agent is an alkaline agent. The hydrolytic agent can be present in the composition as a single hydrolysing agent, or a mixture of hydrolysing agents. Hydrolytic agents described herein can be present in the composition in any amount that can effectively contribute to degradation of a controlled substance. In some embodiments, an hydrolytic agent comprises 0.1 wt. % to 40 wt. % of a total weight of the composition. In other embodiments, the oxidizer comprises 0.1 wt. % to 30 wt. %, 0.1 wt. % to 25 wt. %, 0.1 wt. % to 20 wt. %, 0.1 wt. % to 15 wt. %, 0.1 wt. % to 10 wt. %, 0.5 wt. % to 40 wt. %, 1 wt. % to 40 wt. %, 5 wt. % to 40 wt. %, 8 wt. % to 40 wt. %, 10 wt. % to 40 wt. %, 12 wt. % to 40 wt. %, 15 wt. % to 40 wt. %, 18 wt. % to 40 wt. %, 20 wt. % to 40 wt. %, 25 wt. % to 40 wt. %, 30 wt. % to 40 wt. %, 5 wt. %, 8 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %, 21 wt. %, 22 wt. %, 23 wt. %, 24 wt. %, 25 wt. %, 30 wt. % 35 wt. % or 40 wt. % of a total weight of the composition.

While not intending to be bound by theory, the hydrolytic agent makes the composition basic, which has been observed to increase amine degradation in controlled substances in some cases. However, the compositions have also been observed to operate under acidic conditions to degrade controlled substances, but the presence of acids is believed to accelerated degradation of the oxidizer, thus reducing an amount of oxidizer available to degrade the controlled substances. Particularly, acidic conditions can sometimes reduce the shelf life of the composition hypochlorite generated by oxidizers such as sodium dichloroisocyanurate dehydrate, trichloroisocyanuric acid, and other known hypochlorite producers.

Exemplary hydrolytic agents comprise potassium hydroxide, sodium hydroxide, lithium hydroxide, or combinations thereof.

Compositions described herein can optionally further comprise a deterrent. A deterrent, as described herein, is a substance or compound that imparts an unpleasant effect on one or more of a person's senses. For example, a deterrent can impart a bitter or sour flavor if the composition is consumed. In some cases, a deterrent can cause or induce nausea or vomiting if the composition is consumed. Any deterrent known to skilled artisans can be used, so long as the deterrent is not fatal or does not cause permanent physical injury in the amounts present in the composition. An exemplary embodiment of a deterrent is copper sulfate II.

Deterrents described herein can comprise 0.1 wt. % to 20 wt. % of a total weight of the composition. In some cases, a deterrent can comprise 0.1 wt. % to 18 wt. %, 0.1 wt. % to 16 wt. %, 0.1 wt. % to 14 wt. %, 0.1 wt. % to 12 wt. %, 0.1 wt. % to 10 wt. %, 0.1 wt. % to 8 wt. %, 0.1 wt. % to 6 wt. %, 0.1 wt. % to 5 wt. %, 0.1 wt. % to 3 wt. %, 3 wt. % to 20 wt. %, 5 wt. % to 20 wt. %, 8 wt. % to 20 wt. %, 10 wt. % to 20 wt. %, 12 wt. % to 20 wt. %, 14 wt. % to 20 wt. %, 16 wt. % to 20 wt. %, 18 wt. % to 20 wt. %, 2 wt. %, 3 wt. %, 4 wt. %, 5 wt. %, 6 wt. %, 7 wt. %, 8 wt. %, 9 wt. %, 10 wt. %, 12 wt. %, 13 wt. %, 14 wt. %, or 15 wt. % of a total weight of the composition.

In some embodiments, the composition is a powder. However, in other instances, the composition is a liquid further comprising a solvent, such as an aqueous solvent, an alcohol, or other protic or aprotic solvents. In a preferred embodiment, the composition further comprises water.

II. Degradation Methods

In another aspect, methods of disposing, degrading, or destroying controlled substances, pharmaceutically active agents, and/or pharmaceutically active ingredients is described. In some embodiments, a method of disposing a controlled substance comprises placing a controlled substance in any composition described in Section I herein; and degrading the substance. A previously discussed herein, the controlled substance is irreversibly degraded, non-recoverable, and/or non-retrievable by the composition.

In some cases, the compositions described in Section I are powders, and the method further comprises adding a solvent to the composition and controlled substance mixture. The resulting solvated mixture can optionally be shaken or stirred to distribute the components. The oxidizer and other components in the composition then degrade the controlled substance. In some cases, the solvent is added to the composition, and the controlled substance is subsequently added.

The controlled substance can be in the form of a tablet, capsule, powder, liquid, or any other commonly known form. In cases where the controlled substance is in the form of a tablet or capsule, the tablet or capsule can be added directly to the composition, or the tablet or capsule can be crushed or broken prior to being added to the composition.

In some instances, degradation of the controlled substance is by oxidation, hydrolysis, or both. For example, in some cases the controlled substance can be oxidized by the oxidizer, and the oxidized product then hydrolyzed by the hydrolytic agent into small components that cannot easily or routinely be recombined or converted to form the original controlled substance. Alternatively, the controlled substance can be hydrolyzed by the hydrolytic agent and then subsequently oxidized by the oxidizer to form small components that cannot easily or routinely be recombined or converted to form the original controlled substance. Furthermore, in some instances the controlled substance is irreversibly degraded by oxidation or hydrolysis alone. These are merely exemplary chemical degradation steps, and should not be considered limiting. The skilled artisan would readily recognize that the reactive components in the composition can undergo many different types of chemical reactions based on the particular components comprising the composition, with the final product being an irreversibly degraded controlled substance.

A controlled substance can be irreversibly degraded in the composition within 15 minutes to 10 hours. In some embodiments, a controlled substance can be irreversibly degraded in the composition within 15 min, 30 min, 45 min, 1 hr, 2 hrs, 3 hrs, 4 hrs, 5 hrs, 6 hrs, 7 hrs, 8 hrs, 9 hrs, 10 hrs, or more than 10 hours. In a preferred embodiment, the controlled substance is irreversibly degraded in the composition within 30 min to 1 hr. In a more preferred embodiment, the controlled substance is irreversibly degraded in the composition within 2 hours.

In some embodiments, a method described herein further comprises solidifying the degraded controlled substance and the composition. For example, as the controlled substance is degraded into smaller chemical components, these components can be absorbed by an immobilizer described herein. Additionally, in some cases the immobilizer can absorb the added solvent, and the solidifier can form a solid waste product as the solvent is absorbed.

In some embodiments, the composition described herein can be formed into a tablet, "puck," or wrapped in a sealed packet, such as a polyvinyl alcohol packet. To use a composition described herein with a liquid controlled substance, the composition, in the form of a tablet or "puck", is placed into the liquid controlled substances. Gravity can assist in the mixing of the composition with the controlled substance. The immobilizer, such as a SAP or xanthan gum, can have an uptake time that is greater than a time required to degrade the controlled substance. In some embodiments, solidification (i.e. uptake time of the immobilizer) is about 30 min, 1 hr, 2 hrs, 3 hrs, or more than 3 hrs, which provides enough time for the reactive components of the composition to interact with and degrade the controlled substance before solidification.

Some embodiments described herein are further illustrated in the following non-limiting examples.

Example 1

Preparation of Controlled Substance Standards

Stock solutions of amphetamine, butorphanol, cocaine, codeine, diazepam, fentanyl, glycopyrrolate, hydrocodone, hydromorphone, ketamine, lorazepam, meperidine, methadone, methamphetamine, midazolam, morphine, nalbuphine, oxycodone, pentobarbital, propofol, remifentanil, sufentanil, and Δ9-tetrahydrocannabinol (THC) were prepared with concentrations of 100 µg/mL in methanol (MeOH), or water in cases of cocaine HCl and meperidine. Remifentanil and sufentanil stocks were prepared at a lower concentration of 100 µg/mL, with these being diluted to 10 µg/mL in MeOH (at the 10 µg/mL concentration).

Example 2

Effects of Different Oxidants on Fentanyl and Morphine

Degradation of fentanyl and morphine were tested using a variety of different oxidant classes. The oxidants that were provided in solid form were diluted in water. As the solubility of each compound varied, the concentration of the solutions were different for each compound and are listed in Table 1. Fentanyl and morphine 1 mg/mL standards were diluted to 100 µg/mL in HPLC-grade methanol. Approximately 500 µL of each oxidant solution was combined with 500 µL of fentanyl and morphine solutions, in separate vials. Water was used as a standard. In the cases of nitric acid and peracetic acid, only 250 µL were added to the vials of morphine and fentanyl dilutions. Each of the vials were capped and shaken and left on the bench for approximately 2 hours. Samples containing nitric acid and peracetic acid were neutralized by the addition of 250 µL potassium hydroxide (KOH) solution. All samples were then filtered through 0.45 µm RC syringe filters and placed in fresh HPLC vials. The results are shown in Table 1, which show that 1% $KMNO_4$, 8.25% sodium hypochlorite (household bleach), and 32% peracetic acid effectively denatured/degraded both fentanyl and morphine, whereas other oxidant classes had varying degrees of denaturation/degradation. The results are shown in Table 1.

TABLE 1

Effects of Different Classes of Oxidants on Fentanyl and Morphine

| OXIDANT | CLASS | % SOLUTION CONCENTRATION | % FENTANYL DENATURED | % MORPHINE DENATURED |
|---|---|---|---|---|
| Potassium Permanganate | Permanganates | 1% | 100% (fully denatured) | 100% |
| Hydrogen peroxide | Peroxides | 30% | 10% | 20% |
| Sodium hypochlorite | Hypochlorite | 10-15% available chlorine | 50% | 100% |
| Household bleach | Hypochlorite | 8.25% sodium hypochlorite | 100% | 100% |
| Potassium nitrate | Nitrates | 5% | 0% (no denaturing) | 100% |
| Sodium nitrite | Nitrites | 60% | 0% | 85% |
| Nitric acid | Oxidizing acids | 68% | 5% | 100% |
| Sodium chlorate | Chlorates | 60% | 0% | 100% |
| Sodium chlorite | Chlorites | 5% | 0% | 90% |
| Sodium perchlorate | Perchlorates | 60% | 0% | 100% |
| Potassium chromate | Chromates | 50% | 0% | 10% |
| Potassium dichromate | Dichromates | 2% | 0% | 20% |
| Ruthenium tetroxide | Tetroxides | 0.5% | 12% | 100% |
| Sodium perborate | Perborates | 1% | 0% | 0% |
| Potassium iodate | Iodates | 2.5% | 0% | 0% |
| Peracetic acid | Peroxy acids | 32% | 99% | 100% |
| Potassium bromate | Bromates | 2% | 0% | 0% |
| Sodium periodate | Periodates | 10% | 0% | 85% |
| Sodium persulfate | Persulfates | 40% | 0% | 85% |

Example 3

Degradation of Controlled Substances in $KMnO_4$

Degradation of fentanyl, morphine, methadone, oxycodone, nalbuphine, lorazepam, Δ9-tetrahydrocannabinol (THC), glycopyrrolate, ketamine, amphetamine, methamphetamine, pentobarbital, cocaine (in water), cocaine (in methanol), diazepam, meperidine (in water), and meperidine (in methanol) were tested using potassium permanganate ($KMnO_4$). The 100 µg/mL dilutions of each controlled substance were prepared according to Example 1, and were treated with 1% $KMnO_4$ in water or purified water (as a control) for approximately 2 hours. Each of the vials were capped and shaken and left on the bench for approximately 2 hours. All samples were then filtered through 0.45 µm RC syringe filters and placed in fresh HPLC vials. The results are shown in Table 2, which show that 1% KMNO$_4$ effectively denatured/degraded fentanyl, morphine, methadone, oxycodone, nalbuphine, lorazepam, Δ9-tetrahydrocannabinol (THC), and glycopyrrolate. However, 1% KMNO$_4$ was unable to completely denature/degrade ketamine, amphetamine, methamphetamine, pentobarbital, cocaine (in water), cocaine (in methanol), diazepam, meperidine (in water), and meperidine (in methanol)

TABLE 2

Degradation of Controlled Substances Treated with 1% KMnO$_4$

| Controlled Substance | % Denatured |
|---|---|
| fentanyl | 100% |
| morphine | 100% |
| methadone | 100% |
| oxycodone | 100% |
| nalbuphine | 100% |
| lorazepam | 100% |
| Δ9-tetrahydrocannabinol (THC) | 100% |
| glycopyrrolate | 100% |
| ketamine | <20% |
| amphetamine | 0% |
| methamphetamine | <20% |
| pentobarbital | 0% |
| cocaine (in water) | 0% |
| cocaine (in methanol) | 0% |
| diazepam | 10% |
| meperidine (in water) | <25% |
| meperidine (in methanol) | <25% |

Example 4

Degradation of Controlled Substances in KMnO$_4$ and KOH

Degradation of fentanyl, morphine, methadone, oxycodone, nalbuphine, lorazepam, Δ9-tetrahydrocannabinol (THC), and glycopyrrolate were tested using a combination of KMnO$_4$ and KOH. Stock 100 μg/mL dilutions of each controlled substance prepared according to Example 1. Approximately 50 μL of each stock dilution were added to two separate vials. 350 μL water, 500 μL 1% KMnO$_4$, and 500 μL 60% KOH were added to one of the vials. Approximately 1.3 mL water was to each of the second vials as a standard. The vials were left on the bench for 2 hours. Each of the vials containing KOH was neutralized with 500 μL HCl, and the standard vials each received 500 μL water. All samples were then filtered through 0.45 μm RC syringe filters and placed in fresh HPLC vials. The samples were analyzed with LC-MS. The results are shown in Table 3, which show that KMnO$_4$ and KOH effectively denatured/degraded fentanyl, morphine, methadone, oxycodone, nalbuphine, lorazepam, Δ9-tetrahydrocannabinol (THC), and glycopyrrolate.

TABLE 3

Degradation of Controlled Substances Treated with A Mixture of KMnO$_4$ and KOH

| CONTROLLED SUBSTANCE | % DENATURED |
|---|---|
| fentanyl | 100% |
| morphine | 100% |
| methadone | 100% |
| oxycodone | 100% |
| nalbuphine | 100% |
| lorazepam | 100% |
| Δ9-tetrahydrocannabinol (THC) | 100% |
| glycopyrrolate | 100% |

Example 5

Degradation of Controlled Substances in Halogenated Oxidants

Dilutions of 100 μg/mL of amphetamine, cocaine, diazepam, ketamine, meperidine, methamphetamine, and pentobarbital were prepared according to Example 1. Each of these controlled substances displayed limited degradation in the presence of 1% KMnO$_4$. Each of the standards were diluted to 100 μg/mL in HPLC-grade methanol, and also water in the case of cocaine and meperidine. A solution of trichloroisocyanuric acid (TCI) was diluted in water to make a 0.5% solution, and sodium dichloroisocyanurate dihydrate (DCI) was diluted in water to make a 20% solution. A solution of 5.25% of sodium hypochlorite solution was obtained using household bleach. Approximately 500 μL of each 100 μg/mL drug dilutions were each placed in 4 separate vials. Vial 1 of 4 received 500 μL household bleach. Vial 2 of 4 received 500 μL 20% DCI. Vial 3 of 4 received 500 μL 0.5% TCI. Vial 4 of 4 received 500 μL water, as a control. The vials were capped, shaken and left on the bench for approximately 2 hours. All samples were then filtered through 0.45 μm RC syringe filters and placed in fresh HPLC vials. Approximately 500 μL of HPLC-grade methanol were added to each vial, and the samples were analyzed with LC-MS. The results are shown in Table 4, which show that sodium hypochlorite, DCI, and TCI effectively denatured/degraded many of the controlled substances that were inert to 1% KMnO$_4$.

TABLE 4

Degradation of Controlled Substances treated with sodium hypochlorite, DCI, and TCI

| CONTROLLED SUBSTANCE | 5.25% Sodium Hypochlorite | 20% DCI | 0.5% TCI |
|---|---|---|---|
| ketamine | 90% | 100% | 100% |
| amphetamine | 100% | 100% | 100% |
| methamphetamine | 90% | 100% | 100% |
| pentobarbital | 100% | 95% | 50% |
| cocaine (in water) | 100% | 100% | 50% |
| cocaine (in methanol) | 90% | 100% | 0% |
| diazepam | 100% | 100% | 100% |
| meperidine (in water) | 100% | 100% | 100% |
| meperidine (in methanol) | 100% | 100% | 100% |

Example 6

Degradation of Controlled Substances in KMnO$_4$, Sodium Dichloroisocyanurate Dehydrate, and Trichloroisocyanuric Acid Dilutions of 100 μg/mL of amphetamine, butorphanol, cocaine, codeine, diazepam, fentanyl, hydrocodone, hydromorphone, ketamine, lorazepam, meperidine, methadone, methamphetamine, midazolam, morphine, nalbuphine, oxycodone, pentobarbital, propofol, remifentanil, sufentanil, and THC were prepared according to Example 1, except for remifentanil and sufentanil, which were provided as 100 μg/mL standards and were diluted to 10 μg/mL in HPLC-grade methanol. Approximately 500 μm of each drug dilution were placed in 3 separate vials. Vial 1 of 3 then received 990 μL at water as a standard control, vial 2 of 3 received 330 μL $KMnO_4$, 330 μL 0.5% TCI, and 330 μL 0.5% DCI, and vial 3 of 3 received 330 μL % $KMnO_4$, 330 μL 0.5% TCI, and 330 μL 20% DCI. The vials were capped and shaken and left on the bench for approximately 2 hours. Then all samples were filtered through 0.45 μm RC syringe filters before analysis with LC-MS. The results are shown in Table 5, which show that 0.5% DCI, in combination with 0.5% TCI and 1% $KMnO_4$, was sufficient to denature all of the drugs on the list except cocaine and pentobarbital within 2 hours. 20% DCI in combination with 0.5% TCI and 1% $KMnO_4$ fully denatured cocaine and denatured approximately 90% of the pentobarbital within 2 hours.

TABLE 5

Degradation of Controlled Substances treated with $KMnO_4$, DCI, and TCI

| CONTROLLED SUBSTANCE | % Denatured in 1% $KMnO_4$, 0.5% TCI and 0.5% DCI | % Denatured in 1% $KMnO_4$, 0.5% TCI, and 20% DCI |
| --- | --- | --- |
| Amphetamine | 100% | 100% |
| Butorphanol | 100% | 100% |
| Cocaine | 0% | 100% |
| Codeine | 100% | 100% |
| Diazepam | 100% | 100% |
| Fentanyl | 100% | 100% |
| Hydrocodone | 100% | 100% |
| Hydromorphone | 100% | 100% |
| Ketamine | 100% | 100% |
| Lorazepam | 100% | 100% |
| Meperidine | 100% | 100% |
| Methadone | 100% | 100% |
| Methamphetamine | 100% | 100% |
| Midazolam | 100% | 100% |
| Morphine | 100% | 100% |
| Nalbuphine | 100% | 100% |
| Oxycodone | 100% | 100% |
| Pentobarbital | 50% | 90% |
| Propofol | 100% | 100% |
| Remifentanil | 100% | 100% |
| Sufentanil | 100% | 100% |
| THC | 100% | 100% |

Example 7

Degradation of Controlled Substances in $KMnO_4$, Sodium Dichloroisocyanurate Dehydrate, and Trichloroisocyanuric Acid in the Presence of Immobilizers and Solidifiers Six formulations were tested as denaturants of fentanyl, ketamine and morphine. Each formulation contained 2 mL 1% $KMnO_4$, 2 mL 0.5% TCI, and 2 mL 20% DCI, as well as the following ingredients:
  Formulation 1: 1 g xanthan gum;
  Formulation 2: 0.5 g xanthan gum+0.5 g clay;
  Formulation 3: 0.75 g micronized cellulose and 0.25 g calcium chloride;
  Formulation 4: 0.25 g xanthan gum+0.25 g fumed silica+0.25 g sand+0.25 g clay;
  Formulation 5: 0.25 g micronized cellulose+0.25 g fumed silica+0.25 g sand+0.25 g clay; and
  Formulation 6: 1 g micronized cellulose.

Fentanyl, morphine, and ketamine standards were diluted to 100 μg/mL in HPLC-grade methanol according to Example 1. Approximately 500 μL of 100 μg/mL ketamine, fentanyl, and morphine were placed in separate vials. 500 mg of each of Formulations 1-6 were placed in vials containing the ketamine, fentanyl, and morphine. Vials having only ketamine, fentanyl, or morphine without any of the Formulations were used as controls. The vials were capped and left on the bench for approximately 2 hours. Then, 1.5 mL of methanol were placed in each vial, and the vials were shaken and the solids were allowed to settle to the bottom. The liquid on top was then removed, filtered through 0.45 μRC syringe filters, and placed in HPLC vials. The samples were analyzed with LC-MS. The results are shown in Table 6, which show that $KMnO_4$, DCI, and TCI in combination with various immobilizers and stabilizers effectively denatured/degraded many of the controlled substances, with Formulations 4 and 5 being the most effective.

TABLE 6

Degradation of Controlled Substances with Oxidizers, Immobilizers, and Stabilizers

| Controlled Substance | Formulation 1 | Formulation 2 | Formulation 3 | Formulation 4 | Formulation 5 | Formulation 6 |
| --- | --- | --- | --- | --- | --- | --- |
| Fentanyl | 0% | 0% | 0% | 100% | 100% | 5% |
| Morphine | 75% | 98% | 99% | 100% | 100% | 100% |
| Ketamine | 0% | 0% | 0% | 100% | 100% | 97% |

*The % is the amount of controlled substance denatured after two hours.

Example 8

Degradation of Controlled Substances: Comparative Data

A third party was contracted to prepare 100 μg/mL dilutions of fentanyl, morphine, and ketamine according to Example 1. These controlled substances were treated with Composition 1 comprising: 330 μL of 1% KMnO$_4$ in water, 330 μL of 20% sodium dichloroisocyanurate dehydrate (DCI), and 330 μL, of 0.5% trichloroisocyanuric acid (TCI) for approximately 2 hours. Purified water was used as a control. The three controlled substances were additionally treated with nine different commercially available branded products, the branded products having the following active ingredients:

Brand 1: activated charcoal and liquid dissolving agent.
Brand 2: 25% activated charcoal.
Brand 3: water-based proprietary blend of ingredients.
Brand 4: calcium hypochlorite, Fuller's earth, and an absorbent polymer.
Brand 5: organic plant-based powder.
Brand 6: proprietary mixture of denaturants and deterrents.
Brand 7: activated charcoal.
Brand 8: Bentonite clay.
Brand 9: Activated Charcoal The active ingredients of Brands 1-9 were combined with the 100 μg/mL dilutions of fentanyl, morphine, and ketamine. The vials were shaken and left out on the bench for approximately 2 hours. Each of the samples were then filtered and tested using LC-MS. The results are shown in Table 7. As shown, Composition 1 successfully denatured/degraded 100% of each of fentanyl, morphine, and ketamine. In contrast, none of the commercial products were able to denature/degrade 100% of any of the controlled substances, with many showing no degradation at all.

TABLE 7

Comparative Data

| Product | % Denaturation of Fentanyl | % Denaturation of Morphine | % Denaturation of Ketamine |
|---|---|---|---|
| Composition 1 | 100% | 100% | 100% |
| Brand 1 | 0% | 0% | 15% |
| Brand 2 | 5% | 0% | 0% |
| Brand 3 | 70% | 70% | 0% |
| Brand 4 | 5% | 25% | 0% |
| Brand 5 | 0% | 0% | 0% |
| Brand 6 | 0% | 33% | 85% |
| Brand 8 | 10% | 60% | 10% |
| Brand 8 | 25% | 33% | 10% |
| Brand 9 | 15% | 60% | 0% |

Although the above description and the attached claims disclose a number of embodiment of the invention, other alternative aspects of the invention are disclosed in the following further embodiments.

Embodiment 1. A composition, comprising: an oxidizer; and a hydrolytic agent.

Embodiment 2. The composition of Embodiment 1, wherein the oxidizer is potassium permanganate, sodium hypochlorite, a halogenated oxidant, hydrogen peroxide, nitric acid, sulfuric acid, sodium perborate tetrahydrate, sodium pyrophosphate tetrabasic, or mixtures thereof.

Embodiment 3. The composition of Embodiment 1, wherein the oxidizer is potassium permanganate.

Embodiment 4. The composition of Embodiment 1, wherein the hydrolytic agent is an alkaline agent.

Embodiment 5. The composition of Embodiment 1, wherein the hydrolytic agent is potassium hydroxide, sodium hydroxide, lithium hydroxide, or combinations thereof.

Embodiment 6. The composition of Embodiment 1, further comprising a binding agent.

Embodiment 7. The composition of Embodiment 6, wherein the binding agent comprises a gelatin, an agarose, a starch, a fumed silica, a vegetable gum, a clay, a cellulose, a saccharide, or mixtures thereof.

Embodiment 8. The composition of Embodiment 7, wherein the saccharide comprises sucrose.

Embodiment 9. The composition of Embodiment 1, further comprising an absorbent to solidify the mixture.

Embodiment 10. The composition of Embodiment 9, wherein the absorbent is a polymer.

Embodiment 11. The composition of Embodiment 10, wherein the polymer is a super absorbent polymer.

Embodiment 12. The composition of Embodiment 11, wherein the super absorbent polymer comprises a polyacrylate.

Embodiment 13. The composition of Embodiment 1, further comprising a deterrent.

Embodiment 14. The composition of Embodiment 13, wherein the deterrent is copper sulfate II.

Embodiment 15. The composition of Embodiment 1, wherein the oxidizer comprises 0.1 wt. % to 50 wt. % of a total weight of the composition.

Embodiment 16. The composition of Embodiment 1, wherein the hydrolytic agent comprises 0.1 wt. % to 50 wt. %. of a total weight of the composition.

Embodiment 17. The composition of Embodiment 6, wherein the binding agent comprises 0.1 wt. % to 20 wt. % of a total weight of the composition.

Embodiment 18. The composition of Embodiment 9, wherein the absorbent comprises 25 wt. % to 75 wt. % of a total weight of the composition.

Embodiment 19. A method of disposing of controlled substances, comprising: placing a Drug Enforcement Agency identified schedule I, II, and/or III controlled substance in the composition of any of Embodiments 1-18; and degrading the substance.

Embodiment 20. The method of Embodiment 19, further comprising solidifying the degraded substance and the composition.

Embodiment 21. The method of Embodiment 19, wherein the substance is irreversibly degraded.

Embodiment 22. The method of Embodiment 19, wherein the substance is degraded by oxidation, hydrolysis, or both.

Embodiment 23. The method of Embodiment 19, wherein the substance is degraded in the composition within 15 minutes to 10 hours.

Embodiment 24. The method of Embodiment 19, wherein the substance is degraded in the composition within 1 hour to 6 hours.

Embodiment 25. A composition for decomposing controlled substances, comprising: up to 30 wt. % oxidizer; and up to 30 wt. % immobilizer; wherein the wt. % is based on a total weight of the composition.

Embodiment 26. The composition of Embodiment 25, wherein the oxidizer comprises one or more of a permanganate and a halogenated oxidant.

Embodiment 27. The composition of Embodiment 26, wherein the permanganate comprises potassium permanganate.

Embodiment 28. The composition of Embodiment 26, wherein the halogenated oxidant comprises sodium dichloroisocyanurate dihydrate, sodium dichloroisocyanurate, potassium dichloroisocyanurate dihydrate, trichloroisocyanuric acid, dichloroisocyanuric acid, or any combination thereof.

Embodiment 29. The composition of Embodiment 26, wherein the oxidizer comprises: 0.1 to 8 wt. % potassium permanganate; 0.1 to 25 wt. % sodium dichloroisocyanurate dehydrate; and 0.1 to 7 wt. % trichloroisocyanuric acid.

Embodiment 30. The composition of Embodiment 25, wherein the immobilizer comprises a gelatin, an agarose, a starch, a vegetable gum, a cellulose, a cellulose derivative, a carbomer, a polyvinylpyrrolidone, polyethylene oxide, polyethylene glycol, an alginate, guar gum, xanthan gum, a saccharide, an amylopectin, Arabic gum, a polyacrylic acid, or any combination thereof.

Embodiment 31. The composition of Embodiment 25, wherein the immobilizer comprises xanthan gum.

Embodiment 32. The composition of Embodiment 25, wherein the xanthan gum comprises 8-30 wt. % of the composition.

Embodiment 33. The composition of Embodiment 32, further comprising a multivalent alkaline earth metal-based chloride.

Embodiment 34. The composition of Embodiment 33, wherein the multivalent alkaline earth metal-based chloride is $CaCl_2$ present up to 5 wt. % of the composition.

Embodiment 35. The composition of Embodiment 25, further comprising a solidifier comprising a clay, a fumed silica, a sand, or any combination thereof.

Embodiment 36. The composition of Embodiment 35, wherein the clay is present up to 25 wt. %; the fumed silica is present up to 25 wt. %; and/or the sand is present up to 25 wt. %.

Embodiment 37. A composition comprising: up to 30 wt. % xanthan gum; up to 8 wt. % potassium permanganate; 0.1 to 25 wt. % sodium dichloroisocyanurate dehydrate; and 0.1 to 7 wt. % trichloroisocyanuric acid; wherein the wt. % is based on a total weight of the composition.

Embodiment 38. The composition of Embodiment 37, further comprising one or more of: up to 25 wt. % clay; up to 25 wt. % fumed silica; and up to 25 wt. % sand.

Embodiment 39. The composition of Embodiment 37, further comprising up to 7 wt. % of $CaCl_2$.

Embodiment 40. A method of degrading a pharmaceutically active ingredient, comprising placing the pharmaceutically active ingredient in the composition of Embodiment 1; and degrading the pharmaceutically active ingredient.

Embodiment 41. The method of Embodiment 40, wherein the pharmaceutically active ingredient is a US Drug Enforcement Agency identified schedule I, II, and/or III controlled substance.

Embodiment 42. The method of Embodiment 40, wherein degrading the pharmaceutically active ingredient comprising rendering the pharmaceutically active ingredient non-retrievable as defined by the US Drug Enforcement Agency under 21 C.F.R. § 1300.05.

Embodiment 43. The method of Embodiment 40, further comprising adding water to the composition of Embodiment 1.

Embodiment 44. The method of Embodiment 40, wherein the pharmaceutically active ingredient is degraded within two hours after being placed in the composition of Embodiment 1.

Those skilled in the art of chemical denaturing and controlled substance handling and disposal will appreciate that many modifications and substitution may be made to the foregoing description without departing from the spirit and scope of the present disclosure.

What is claimed is:

1. A composition for decomposing controlled substances, comprising:
   an oxidizer an oxidizer comprising potassium permanganate in combination with:
     sodium dichloroisocyanurate dihydrate, potassium dichloroisocyanurate dihydrate, trichloroisocyanuric acid, dichloroisocyanuric acid, or any combination thereof; and
   up to 30 wt. % immobilizer;
   wherein the wt. % is based on a total weight of the composition.

2. The composition of claim 1, wherein the oxidizer comprises potassium permanganate, sodium dichloroisocyanurate dehydrate, and trichloroisocyanuric acid.

3. The composition of claim 2, wherein the oxidizer comprises:
   0.1 to 8 wt. % potassium permanganate;
   up to 25 wt. % sodium dichloroisocyanurate dehydrate; and
   up to 7 wt. % trichloroisocyanuric acid.

4. The composition of claim 1, wherein the immobilizer comprises a gelatin, an agarose, a starch, a vegetable gum, a cellulose, a cellulose derivative, a carbomer, a polyvinylpyrrolidone, polyethylene oxide, polyethylene glycol, an alginate, guar gum, xanthan gum, a saccharide, an amylopectin, Arabic gum, a polyacrylic acid, or any combination thereof.

5. The composition of claim 1, wherein the immobilizer comprises xanthan gum.

6. The composition of claim 5, wherein the xanthan gum comprises 8-30 wt. % of the composition.

7. The composition of claim 6, further comprising a multivalent alkaline earth metal-based chloride.

8. The composition of claim 7, wherein the multivalent alkaline earth metal-based chloride is $CaCl_2$, $MgCl_2$, $BaCl_2$, or mixtures thereof present up to 5 wt. % of the composition.

9. The composition of claim 1, further comprising a solidifier comprising a clay, a silica, a sand, or any combination thereof.

10. The composition of claim 9, wherein the clay is present up to 25 wt. %; the silica is present up to 25 wt. %; and/or the sand is present up to 25 wt. %.

11. A composition comprising:
    up to 8 wt. % potassium permanganate;
    up to 25 wt. % sodium dichloroisocyanurate dehydrate; and
    up to 7 wt. % trichloroisocyanuric acid;
    wherein the wt. % is based on a total weight of the composition.

12. The composition of claim 11, further comprising one or more of:
    up to 25 wt. % clay;
    up to 25 wt. % silica; and
    up to 25 wt. % sand.

13. The composition of claim 11, further comprising up to 7 wt. % of $CaCl_2$, $MgCl_2$, $BaCl_2$, or mixtures thereof.

* * * * *

UNITED STATES PATENT AND TRADEMARK OFFICE
CERTIFICATE OF CORRECTION

| | |
|---|---|
| PATENT NO. | : 10,668,312 B2 |
| APPLICATION NO. | : 16/456958 |
| DATED | : June 2, 2020 |
| INVENTOR(S) | : Justin Stas et al. |

It is certified that error appears in the above-identified patent and that said Letters Patent is hereby corrected as shown below:

On the Title Page

Under abstract "13 Claims, No Drawing Sheets" should read --18 Claims, No Drawing Sheets--.

In the Claims

Column 20, Line 64, (approx.) insert the following claims after Claim 13:
--14. A method of degrading a pharmaceutically active ingredient, comprising:
  placing the pharmaceutically active ingredient in the composition of claim 1; and
  degrading the pharmaceutically active ingredient.

15. The method of claim 14, wherein the pharmaceutically active ingredient is a US Drug Enforcement Agency identified schedule I, II, and/or III controlled substance.

16. The method of claim 14, wherein degrading the pharmaceutically active ingredient comprising rendering the pharmaceutically active ingredient non-retrievable as defined by the US Drug Enforcement Agency under 21 C.F.R. § 1300.05.

17. The method of claim 14, further comprising adding water to the composition of claim 1.

18. The method of claim 14, wherein the pharmaceutically active ingredient is degraded within two hours after being placed in the composition of claim 1.--.

Signed and Sealed this
Twenty-eighth Day of July, 2020

Andrei Iancu
*Director of the United States Patent and Trademark Office*